US008697839B2

(12) United States Patent
Li et al.

(10) Patent No.: US 8,697,839 B2
(45) Date of Patent: Apr. 15, 2014

(54) GQ PROTEIN COMPETITIVE INHIBITORY POLYPEPTIDES, PREPARATION METHODS AND USES THEREOF

(75) Inventors: Xiaohui Li, Chongqing (CN); Haigang Zhang, Chongqing (CN); Jianzhi Zhou, Chongqing (CN); Shuhui Li, Chongqing (CN)

(73) Assignees: Xiaohui Li, Chongqing (CN); Third Military Medical University, Chongqing (CN); Chongqing Zhaokanglihui Meditech Co., Ltd., Chongqing (CN); Chongqing Qingyang Pharmaceutical Co., Ltd., Chongqing (CN)

( * ) Notice: Subject to any disclaimer, the term of this patent is extended or adjusted under 35 U.S.C. 154(b) by 0 days.

(21) Appl. No.: 13/058,836

(22) PCT Filed: Aug. 11, 2008

(86) PCT No.: PCT/CN2008/001449
§ 371 (c)(1),
(2), (4) Date: Aug. 17, 2011

(87) PCT Pub. No.: WO2010/017653
PCT Pub. Date: Feb. 18, 2010

(65) Prior Publication Data
US 2012/0065139 A1  Mar. 15, 2012

(51) Int. Cl.
*C07K 14/47* (2006.01)
*A61P 9/00* (2006.01)
*C12N 15/12* (2006.01)

(52) U.S. Cl.
USPC .......................... 530/324; 514/16.4; 514/20.6

(58) Field of Classification Search
None
See application file for complete search history.

(56) References Cited

U.S. PATENT DOCUMENTS

2006/0018919 A1* 1/2006 Gu .............................. 424/190.1
2006/0166872 A1* 7/2006 Jabbour et al. .................. 514/12

FOREIGN PATENT DOCUMENTS

| WO | WO 99/05294 | 2/1999 |
| WO | WO 99/32640 | 7/1999 |
| WO | WO 02/36622 | 5/2002 |
| WO | WO 02/072778 | 9/2002 |

OTHER PUBLICATIONS

Record for Accession No. 2011:1589732, CAPLUS database, 2011, no author listed.*
Aoki et al., Myosin light chain kinase mediates sarcomere organization during cardiac hypertrophy in vitro, Nat. Med., 6(2):183-188 (2000).
Berenji et al. Does load-induced ventricular hypertrophy progress to systolic heart failure? Am J Physiol Heart Circ Physiol., 289(1): H8-H16 (2005).
Carlstrom et al. A quercetin supplemented diet does not prevent cardiovascular complications in spontaneously hypertensive rats. J. Nutr., 137(3):628-633(2007).
Cooper, Basic determinants of myocardial hypertrophy: a review of molecular mechanisms. Annu. Rev. Med., 48:13-23 (1997).
Dorn et al., Low- and high-level transgenic expression of β2-adrenergic receptors differentially affect cardiac hypertrophy and function in Gαq-overexpressing mice. Proc Natl. Acad. Sci. USA, 96(11):6400-6405 (1999).
Jalili et al. Quercetin-supplemented diets lower blood pressure and attenuate cardiac hypertrophy in rats with aortic constriction, J. Cardiovasc. Pharmacol., 47(4):531-541 (2006).
McKinsey & Kass, Small-molecule therapies for cardiac hypertrophy: moving beneath the cell surface, Nat. Rev. Drug Discov. 6(8):617-635 (2007).
Mitchell et al. Early recognition and treatment of hypertensive heart disease, Curr. Opin. Cardiol., 20(4):282-289 (2005).
Niizeki et al. Diacylglycerol Kinase zeta Rescues Galphaq-Induced Heart Failure in Transgenic Mice. Circ. J., 72(2): 309-317 (2008).
Zhang, H.G. Optimization of G Protein Inhibitory Polypeptide and Activities on Cardiac Hypertrophy. Chinese Doctoral Dissertations and Master's Theses Full-tex Database (Doctor) Medicin and Health Sciences. Jan. 15, 2006, No. 1, p. E062-5, ISSN 1671-6779.
Zhou, J.Z. et al. Cloning and gene expression of G protein competitive inhibitory polypeptide and its prophylactic effects on myocardial hypertrophy in vitro. Acta Pharmacol. Sin., Nov. 2003, vol. 24, No. 11, pp. 1108-1112, ISSN 1671-4083.
Zhou, J.Z. et al. Construction of expression vector for prophylactic myocardial hypertrophy GCIP polypeptide. Acta Academiae Medicinae Militaris Tertiae, Feb. 2004, vol. 26, No. 4, pp. 298-300, ISSN 1000-5404.
Zhou, J.Z. et al. Construction and expression of G protein competitive inhibitory polypeptide GCIP-27. Chongqing Medicine, Nov. 2007, vol. 36, No. 21, pp. 2172-2173, ISSN 1671-8348.
Zhang, H.G. et al. G(alpha q)-protein carboxyl terminus imitation polypeptide GCIP-27 attenuates cardiac hypertrophy in vitro and in vivo. Clinical and Experimental Pharmacology and Physiology, Dec. 2007, vol. 34, No. 12, pp. 1276-1281, ISSN 0305-1870.
International Search Report and Written Opinion dated May 21, 2009 for PCT Application No. PCT/CN2008/001449, filed Aug. 11, 2008.
Chillar et al., "Structural and Functional Analysis of the C-Terminus of G[alpha]q in Complex with the Human Thromboxane A 2 Receptor Provides Evidence of Constitutive Activity", Biochemistry, vol. 49, No. 30, pp. 6365-6374 (2010).
Conklin B R et al., "Substitution of Three Amino Acids Switches Receptor Specificity of Gq alpha to that of Gi alpha", Nature, vol. 363, No. 6426, pp. 274-276 (1993).

(Continued)

*Primary Examiner* — Zachary Howard
(74) *Attorney, Agent, or Firm* — Knobbe, Martens, Olson & Bear LLP

(57) ABSTRACT

Provided are a series of Gq protein competitive inhibitory polypeptides (GCIPs), polynucleotides encoding them, and preparation methods thereof. Also provided are pharmaceutical compositions comprising GCIP polypeptides and their uses in the manufacture of drugs for treating myocardial hypertrophy.

14 Claims, 3 Drawing Sheets

(56) References Cited

OTHER PUBLICATIONS

Dan-Li Yang et al., "G[alpha]q-Protein Carboxyl Terminus Imitation Polypeptide (GCIP)-27 Inhibits Right Ventricular Hypertrophy Induced by Monocrotaline in Rats", Biological & Pharmaceutical Bulletin, vol. 32, No. 3, pp. 376-381 (2009).

Gilchrist et al., "Galpha Minigenes Expressing C-terminal Peptides Serve as Specific Inhibitors of Thrombin-mediated Endothelial Activation", Journal of Biological Chemistry, vol. 276, No. 28, pp. 25672-25679 (2001).

H. E. Hamm, "The Many Faces of G Protein Signaling", Journal of Biological Chemistry, vol. 273, No. 2, pp. 669-672 (1998).

J. R. Keys et al., "Gq-Coupled Receptor Agonists Mediate Cardiac Hypertrophy Via the Vasculature", Hypertension, vol. 40, No. 5, pp. 660-666 (2002).

Martin et al., "Potent peptide analogues of a G protein receptor-binding region obtained with a combinatorial library", Journal of Biological Chemistry, vol. 271, No. 1, pp. 361-366, (1996).

Sudhiranjan et al., "Cardiac hypertrophy: mechanisms and therapeutic opportunities", Antioxidants & Redox Signaling, vol. 9, No. 6, pp. 623-652 (2007).

Russian Office Action dated Jul. 9, 2012 (and English translation thereof) for Russian Patent Application No. 2011104241/10(005934).

European Official Communication dated Jun. 20, 2012 for European Patent Application No. 08783634.2.

European Extended Search Report dated Oct. 19, 2011 for European Patent Application No. 08783634.2.

Ferrario et al., "Role of the Renin-Angiotensin-Aldosterone System and Proinflammatory Mediators in Cardiovascular Disease", Am. J. Cardiol., 2006, 98(1):121-128.

Rajagopalan et al., "Complete Renin-Angiotension-Aldosterone System (RAAS) Blockade in High-Risk Pateints: Recent Insights From Renine Blockade Studies", Hypertension, 2013, 62(3):444-449.

Communication Under Rule 71(3) EPC "Intent to Grant" dated Feb. 1, 2013 for European Application No. 08 783 634.2.

* cited by examiner

SEQUENCE LISTING

```
<160> NUMBER OF SEQ ID NOS: 26

<210> SEQ ID NO 1
<211> LENGTH: 55
<212> TYPE: PRT
<213> ORGANISM: Homo sapiens

<400> SEQUENCE: 1

Ala Arg Glu Phe Ile Leu Lys Met Phe Val Asp Leu Asn Pro Asp Ser
1               5                   10                  15

Asp Lys Ile Ile Tyr Ser His Phe Thr Cys Ala Thr Asp Thr Glu Asn
            20                  25                  30

Ile Arg Phe Val Phe Ala Ala Val Lys Asp Thr Ile Leu Gln Leu Asn
        35                  40                  45

Leu Lys Glu Tyr Asn Leu Val
    50                  55

<210> SEQ ID NO 2
<211> LENGTH: 45
<212> TYPE: PRT
<213> ORGANISM: Homo sapiens

<400> SEQUENCE: 2

Asp Leu Asn Pro Asp Ser Asp Lys Ile Ile Tyr Ser His Phe Thr Cys
1               5                   10                  15

Ala Thr Asp Thr Glu Asn Ile Arg Phe Val Phe Ala Ala Val Lys Asp
            20                  25                  30

Thr Ile Leu Gln Leu Asn Leu Lys Glu Tyr Asn Leu Val
        35                  40                  45

<210> SEQ ID NO 3
<211> LENGTH: 35
<212> TYPE: PRT
<213> ORGANISM: Homo sapiens

<400> SEQUENCE: 3

Tyr Ser His Phe Thr Cys Ala Thr Asp Thr Glu Asn Ile Arg Phe Val
1               5                   10                  15

Phe Ala Ala Val Lys Asp Thr Ile Leu Gln Leu Asn Leu Lys Glu Tyr
            20                  25                  30

Asn Leu Val
        35

<210> SEQ ID NO 4
<211> LENGTH: 30
<212> TYPE: PRT
```

<213> ORGANISM: Homo sapiens

<400> SEQUENCE: 4

Cys Ala Thr Asp Thr Glu Asn Ile Arg Phe Val Phe Ala Ala Val Lys
1               5                   10                  15

Asp Thr Ile Leu Gln Leu Asn Leu Lys Glu Tyr Asn Leu Val
            20                  25                  30

<210> SEQ ID NO 5
<211> LENGTH: 27
<212> TYPE: PRT
<213> ORGANISM: Homo sapiens

<400> SEQUENCE: 5

Asp Thr Glu Asn Ile Arg Phe Val Phe Ala Ala Val Lys Asp Thr Ile
1               5                   10                  15

Leu Gln Leu Asn Leu Lys Glu Tyr Asn Leu Val
            20                  25

<210> SEQ ID NO 6
<211> LENGTH: 25
<212> TYPE: PRT
<213> ORGANISM: Homo sapiens

<400> SEQUENCE: 6

Glu Asn Ile Arg Phe Val Phe Ala Ala Val Lys Asp Thr Ile Leu Gln
1               5                   10                  15

Leu Asn Leu Lys Glu Tyr Asn Leu Val
            20                  25

<210> SEQ ID NO 7
<211> LENGTH: 20
<212> TYPE: PRT
<213> ORGANISM: Homo sapiens

<400> SEQUENCE: 7

Val Phe Ala Ala Val Lys Asp Thr Ile Leu Gln Leu Asn Leu Lys Glu
1               5                   10                  15

Tyr Asn Leu Val
            20

<210> SEQ ID NO 8
<211> LENGTH: 17
<212> TYPE: PRT
<213> ORGANISM: Homo sapiens

<400> SEQUENCE: 8

Ala Val Lys Asp Thr Ile Leu Gln Leu Asn Leu Lys Glu Tyr Asn Leu
1               5                   10                  15

Val

<210> SEQ ID NO 9
<211> LENGTH: 15
<212> TYPE: PRT
<213> ORGANISM: Homo sapiens

<400> SEQUENCE: 9

Lys Asp Thr Ile Leu Gln Leu Asn Leu Lys Glu Tyr Asn Leu Val
1               5                   10                  15

<210> SEQ ID NO 10
<211> LENGTH: 12
<212> TYPE: PRT

```
<213> ORGANISM: Homo sapiens

<400> SEQUENCE: 10

Ile Leu Gln Leu Asn Leu Lys Glu Tyr Asn Leu Val
1               5                   10

<210> SEQ ID NO 11
<211> LENGTH: 165
<212> TYPE: DNA
<213> ORGANISM: Homo sapiens

<400> SEQUENCE: 11
gcccgagaat tcattctgaa gatgttcgtg gacctgaacc cagacagtga caaaattatc      60
tactcccact tcacgtgtgc cacagacacc gagaatatcc gctttgtctt tgcagccgtc     120
aaggacacca tcctccagct gaacctgaag gagtacaatc tggtc                    165

<210> SEQ ID NO 12
<211> LENGTH: 135
<212> TYPE: DNA
<213> ORGANISM: Homo sapiens

<400> SEQUENCE: 12
gacctgaacc cagacagtga caaaattatc tactcccact tcacgtgtgc cacagacacc      60
gagaatatcc gctttgtctt tgcagccgtc aaggacacca tcctccagct gaacctgaag     120
gagtacaatc tggtc                                                     135

<210> SEQ ID NO 13
<211> LENGTH: 105
<212> TYPE: DNA
<213> ORGANISM: Homo sapiens

<400> SEQUENCE: 13
tactcccact tcacgtgtgc cacagacacc gagaatatcc gctttgtctt tgcagccgtc      60
aaggacacca tcctccagct gaacctgaag gagtacaatc tggtc                    105

<210> SEQ ID NO 14
<211> LENGTH: 90
<212> TYPE: DNA
<213> ORGANISM: Homo sapiens

<400> SEQUENCE: 14
tgtgccacag acaccgagaa tatccgcttt gtctttgcag ccgtcaagga caccatcctc      60
cagctgaacc tgaaggagta caatctggtc                                      90

<210> SEQ ID NO 15
<211> LENGTH: 81
<212> TYPE: DNA
<213> ORGANISM: Homo sapiens

<400> SEQUENCE: 15
gacaccgaga atatccgctt tgtctttgca gccgtcaagg acaccatcct ccagctgaac      60
ctgaaggagt acaatctggt c                                               81

<210> SEQ ID NO 16
<211> LENGTH: 75
<212> TYPE: DNA
<213> ORGANISM: Homo sapiens

<400> SEQUENCE: 16
gagaatatcc gctttgtctt tgcagccgtc aaggacacca tcctccagct gaacctgaag      60
```

```
gagtacaatc tggtc                                                       75

<210> SEQ ID NO 17
<211> LENGTH: 60
<212> TYPE: DNA
<213> ORGANISM: Homo sapiens

<400> SEQUENCE: 17
gtctttgcag ccgtcaagga caccatcctc cagctgaacc tgaaggagta caatctggtc      60

<210> SEQ ID NO 18
<211> LENGTH: 51
<212> TYPE: DNA
<213> ORGANISM: Homo sapiens

<400> SEQUENCE: 18
gccgtcaagg acaccatcct ccagctgaac ctgaaggagt acaatctggt c               51

<210> SEQ ID NO 19
<211> LENGTH: 45
<212> TYPE: DNA
<213> ORGANISM: Homo sapiens

<400> SEQUENCE: 19
aaggacacca tcctccagct gaacctgaag gagtacaatc tggtc                      45

<210> SEQ ID NO 20
<211> LENGTH: 36
<212> TYPE: DNA
<213> ORGANISM: Homo sapiens

<400> SEQUENCE: 20
atcctccagc tgaacctgaa ggagtacaat ctggtc                                36

<210> SEQ ID NO 21
<211> LENGTH: 60
<212> TYPE: DNA
<213> ORGANISM: Artificial Sequence
<220> FEATURE:
<223> OTHER INFORMATION: single-stranded oligonucleotide

<400> SEQUENCE: 21
tcgagctcca tgggtcgaga attcattctg aagatgttcg tcgactaaac gttctctgca      60

<210> SEQ ID NO 22
<211> LENGTH: 52
<212> TYPE: DNA
<213> ORGANISM: Artificial Sequence
<220> FEATURE:
<223> OTHER INFORMATION: single-stranded oligonucleotide

<400> SEQUENCE: 22
gagaacgttt agtcgacgaa catcttcaga atgaattctc gacccatgga gc              52

<210> SEQ ID NO 23
<211> LENGTH: 85
<212> TYPE: DNA
<213> ORGANISM: Artificial Sequence
<220> FEATURE:
<223> OTHER INFORMATION: single-stranded oligonucleotide

<400> SEQUENCE: 23
gaggtcgacc tgaacccaga cagtgacaaa attatctact cccacttcac gtgtgccaca      60
gacaccgaga atatccgctt tgtct                                            85
```

```
<210> SEQ ID NO 24
<211> LENGTH: 85
<212> TYPE: DNA
<213> ORGANISM: Artificial Sequence
<220> FEATURE:
<223> OTHER INFORMATION: single-stranded oligonucleotide

<400> SEQUENCE: 24
tagcccgggg accagattgt actccttcag gttcagctgg aggatggtgt ccttgacggc      60
tgcaaagaca aagcggatat tctcg                                            85

<210> SEQ ID NO 25
<211> LENGTH: 91
<212> TYPE: DNA
<213> ORGANISM: Artificial Sequence
<220> FEATURE:
<223> OTHER INFORMATION: single-stranded oligonucleotide

<400> SEQUENCE: 25
catggacacc gagaatatcc gctttgtctt tgcagccgtc aaggacacca tcctccagct      60
gaacctgaag gagtacaatc tggtctaacc c                                     91

<210> SEQ ID NO 26
<211> LENGTH: 87
<212> TYPE: DNA
<213> ORGANISM: Artificial Sequence
<220> FEATURE:
<223> OTHER INFORMATION: single-stranded oligonucleotide

<400> SEQUENCE: 26
gggttagacc agattgtact ccttcaggtt cagctggagg atggtgtcct tgacggctgc      60
aaagacaaag cggatattct cggtgtc                                          87
```

GQ PROTEIN COMPETITIVE INHIBITORY POLYPEPTIDES, PREPARATION METHODS AND USES THEREOF

RELATED APPLICATIONS

The instant application is a U.S. national phase under 35 U.S.C. §371 of International Application No. PCT/CN2008/001449, entitled GQ PROTEIN COMPETITIVE INHIBITORY POLYPEPTIDES, PREPARATION METHODS AND USES THEREOF, filed Aug. 11, 2008, designating the U.S. and published on Feb. 18, 2010 as WO2010/017653. The content of these applications are herein incorporated by reference in their entireties.

FIELD OF THE INVENTION

The invention relates to a polypeptide. More particularly, the invention relates to a competitive inhibitory peptide against the Gq protein α. The present invention also relates to a method for preparing the polypeptide, a formulation comprising the polypeptide and the use of the polypeptide in manufacture of a drug for reversing myocardial remodeling.

BACKGROUND OF THE INVENTION

Myocardial remodeling (i.e. commonly known as myocardial hypertrophy) refers that the symptom where cardiocytes are constant in quantity but increase in volume. It is an orchestrated response of cardiocytes to various pathological stimuli and can be resulted from stimulation with hemorheological inducements such as hypertension, valvular heart disease, acute myocardial infarction, congenital heart disease and exercise-induced increase in pressure load as well as humoral endocrine substances such as endothelin, angiotensin II, catecholamines, transforming growth factor β, interleukin-1, thereby having extremely high morbility rate[1]. Only for hypertension alone, the morbility rate is 15-20% in the West. Although the rate is slightly lower in China, the number of patients exceeds 150 million. Myocardial hypertrophy can offer certain compensation at the initial stage of the symptom. As the condition progresses, myocardial hypertrophy can lead to impaired heart function through abnormalities such as disordered myocardial fiber rearrangement and dysfunctioned cardiac contractile and the like, and it may further develop into heart failure. Myocardial hypertrophy is a major mortality contributor as it advances heart failure which in turn causes death. Thus, exploration on a specific drug effective in treating and controlling myocardial hypertrophy is not only the subject matter and research hot-spot facing scientists, but also a major public health concern demanding immediate solution around the globe.

To date, there has been no in-clinic therapeutic drug specific for treating myocardial hypertrophy, mainly due to its multiple etiological causes and complex underlying mechanism. Research studies have shown that the stretch stimulation caused by hemorheological changes or the stimulation by a humoral endocrine substance (being reciprocal causation in disease) can induce pathological responses, such as myocardial hypertrophy, interstitial fibrosis, etc., almost all through the corresponding receptor and post-receptor signal transduction events[2]. Based on such a finding, therapies targeting etiological causes for myocardial hypertrophy were attempted using an endothelin antagonist, a hypotensive drug, an angiotensin convertase inhibitor, etc, which proved to be somewhat effective. However, since many factors and receptors are involved in the pathological response, and additionally, the above-described antagonists/inhibitors can induce up-regulation of their corresponding receptors and the increase in compensatory secretion of ligands to other related receptors while suppress the function of a signal molecule, the treatment effect turns out to be very limited[3-6]. Therefore, there is a great need to develop a specific drug useful in prophylaxis and treatment through more fundamental pathways.

G proteins are heterotrimeric GTP binding proteins consisting of subunit α, β, and γ and play a key role in transduction of stimulatory signals from extracellular space into intracellular space. Norepinephrine (NE), endothelin (ET), angiotensin II (Ang II), and the like agonize an $α_1$-AR, an $AT_1$ receptor, and an endothelin receptor, respectively, then activate the effector enzyme, phospholipase C (PLC-β), through Gq family G proteins, which enzyme in turn acts on $PIP_2$ to produce DAG and $IP_3$; and induce embryonic gene expression within a cell commonly via the signal pathway of DAG-PKC-Ras-MAPK and $IP_3$-$Ca^{2+}$-CaN/CaMPKII-NFAT3/GATA-4, resulting in myocardial remodeling. In addition to activating Raf1 through integrins, stretch stimuli may stimulate secretion of AngII, NE, and $ET_1$, and thus is also closely related with Gq. Furthermore, It is observed in experiments that: ① during the pathological process of myocardial remodeling, the Gq signal is significantly excessive, level of which is significantly higher than the physiological Gq signal in normal tissues; both the function and the morphology of the cardiocyte is not significantly altered when Gqα expression is increased two-fold (or below), myocardial hypertrophy and the contractile dysfunction in the heart occur when Gqα expression increased four-fold, the heart failure come about when Gqα expression increased eight-fold; ② over-expression of Gqα gene in a transgenic manner in the heart of a mouse may induce the apparent myocardial hypertrophy and the fatal heart failure in the animal; ③ knock out of Gqa expression in the heart can significantly attenuate the hypertrophic response of the heart to pressure load[7-9]. Thus, it can be seen that the Gqα plays a central role in occurrence and development of myocardial remodeling, and it is considered as a common target for multiple signal pathways and a key signal element for mediating myocardial remodeling/hypertrophy caused by various factors. Therefore, regulation on Gqα is expected to be a novel strategy and maybe a successful way for reversing myocardial remodeling/hypertrophy.

However, transgenic animals are a class of animals into which the exogenous gene is introduced by experimental means, integrated stably within the chromosomal genome and capable of being inherited to their offspring; the principle for breeding transgenic animals is as follows: a gene/fragment of interest tackled with processes in molecular biology is injected into zygotes/preimplantation embryonic cells of experimental animals by various genetic procedures, the injected zygote/preimplantation embryonic cell is further transplanted into the oviduct or uterus of the recipient animal and allowed to develop into a transgenic animal carrying the exogenous gene, and the function of the exogenous gene is annotated by analyzing the integration status of the exogenous gene in the transgenic animal and the phenotype of the transgenic animal, and those genetically engineered animals with excellent quality are bred by typical genetic breeding method. Thus, based on current technology, treating adult-onset myocardial remodeling/hypertrophy in human with transgenic techniques is neither impractical nor rational. Additionally, knocking out expression of Gqα in the heart will result in severely toxic side effects because Gqα also has important physiological functions. Thus, the two strategies and methods described above have no practical applicable value in clinical management of myocardial remodeling/hypertrophy.

For this reason, we have prepared a series of polypeptides with significant activities for reversing myocardial remodeling/hypertrophy by using systematical techniques, such as, molecule design, optimization, genetic engineering, polypeptide preparation, screening for in vitro and in vivo activities, etc.

DISCLOSURE OF THE INVENTION

Given the disadvantages present in the prior art, an objective of the present invention is to provide a series of polypeptides, which not only have therapeutic activities for reversing myocardial hypertrophy, but also can be easily produced with low cost, and ready for industrialization and commercialization.

Another objective of the present invention is to provide a method of making the series of polypeptides, and such a method is simple in procedure, cost-effective, and can yield a series of polypeptide products with high purity and excellent activities for reversing myocardial hypertrophy.

A further objective of the present invention is to provide a formulation product comprising the polypeptide and the use of the polypeptide in manufacture of a drug for treating myocardial remodeling.

For achieving the purpose of the present invention, a polypeptide is provided firstly in the present invention according to the Gqa polypeptide sequence, which has an amino acid sequence as shown in SEQ ID NO: 1 (a pentapentacontapeptide sequence) and exhibits activities for reversing myocardial hypertrophy.

In a preferred embodiment, the polypeptide provided in the present invention is a polypeptide obtained by deleting at least one amino acid residues at any amino acid position from the first amino acid residue at the N-terminal of SEQ ID NO: 1, while maintaining at least 12 amino acid residues at the C-terminal thereof.

In a preferred embodiment, the polypeptide provided in the present invention is a polypeptide as shown in SEQ ID NO: 2 (a pentatetracontapeptide sequence) obtained by deleting the amino acid residues 1 to 10 at the N-terminal of SEQ ID NO: 1.

In a preferred embodiment, the polypeptide provided in the present invention is a polypeptide as shown in SEQ ID NO: 3 (a pentatriacontapeptide sequence) obtained by deleting the amino acid residues 1 to 20 at the N-terminal of SEQ ID NO: 1.

In a preferred embodiment, the polypeptide provided in the present invention is a polypeptide as shown in SEQ ID NO: 4 (a triacontapeptide sequence) obtained by deleting the amino acid residues 1 to 25 at the N-terminal of SEQ ID NO: 1.

In a preferred embodiment, the polypeptide provided in the present invention is a polypeptide as shown in SEQ ID NO: 5 (a heptacosapeptide sequence) obtained by deleting the amino acid residues 1 to 28 at the N-terminal of SEQ ID NO: 1.

In a preferred embodiment, the polypeptide provided in the present invention is a polypeptide as shown in SEQ ID NO: 6 (a pentacosapeptide sequence) obtained by deleting the amino acid residues 1 to 30 at the N-terminal of SEQ ID NO: 1.

In a preferred embodiment, the polypeptide provided in the present invention is a polypeptide as shown in SEQ ID NO: 7 (a icosapeptide sequence) obtained by deleting the amino acid residues 1 to 35 at the N-terminal of SEQ ID NO: 1.

In a preferred embodiment, the polypeptide provided in the present invention is a polypeptide as shown in SEQ ID NO: 8 (a heptadecapeptide sequence) obtained by deleting the amino acid residues 1 to 38 at the N-terminal of SEQ ID NO: 1.

In a preferred embodiment, the polypeptide provided in the present invention is a polypeptide as shown in SEQ ID NO: 9 (a pentadecapeptide sequence) obtained by deleting the amino acid residues 1 to 40 at the N-terminal of SEQ ID NO: 1.

In a preferred embodiment, the polypeptide provided in the present invention is a polypeptide as shown in SEQ ID NO: 10 (a dodecapeptide sequence) obtained by deleting the amino acid residues 1 to 43 at the N-terminal of SEQ ID NO: 1.

The polypeptide provided in the present invention may also be a polypeptide which is derived from substitution, deletion or addition of one or more amino acids in any of the above-described polypeptide sequence and has a function for reversing myocardial remodeling identical or similar to that of the polypeptide with above-described sequence.

The polypeptide provided in the present invention may also be a polypeptide which comprises any of the above-described polypeptide sequence and has functions for reversing myocardial remodeling.

The invention also provides nucleotide sequences encoding for the above-described polypeptides, which are respectively as follows:

a nucleotide sequence as shown in SEQ ID NO: 11, which encodes the polypeptide shown in SEQ ID NO:1;

a nucleotide sequence as shown in SEQ ID NO: 12, which encodes the polypeptide shown in SEQ ID NO:2;

a nucleotide sequence as shown in SEQ ID NO: 13, which encodes the polypeptide shown in SEQ ID NO:3;

a nucleotide sequence as shown in SEQ ID NO: 14, which encodes the polypeptide shown in SEQ ID NO:4;

a nucleotide sequence as shown in SEQ ID NO: 15, which encodes the polypeptide shown in SEQ ID NO:5;

a nucleotide sequence as shown in SEQ ID NO: 16, which encodes the polypeptide shown in SEQ ID NO:6;

a nucleotide sequence as shown in SEQ ID NO: 17, which encodes the polypeptide shown in SEQ ID NO:7;

a nucleotide sequence as shown in SEQ ID NO: 18, which encodes the polypeptide shown in SEQ ID NO:8;

a nucleotide sequence as shown in SEQ ID NO: 19, which encodes the polypeptide shown in SEQ ID NO:9;

a nucleotide sequence as shown in SEQ ID NO: 20, which encodes the polypeptide shown in SEQ ID NO:10.

The invention also provides a recombinant vector comprising any one of the above-described nucleotide sequence.

In another preferred embodiment, the recombinant vector comprises a T7 promoter.

In a preferred embodiment, the recombinant vector comprises the nucleotide sequences and the plasmid pIVEX2.3MCS.

The present invention also provides a formulation comprising polypeptides set forth above and pharmaceutically acceptable additives.

In a preferred embodiment, the formulation is a parenteral injection.

In another aspect, the present invention provides the use of the above-described polypeptide in manufacture of a drug for treating myocardial hypertrophy.

In a preferred embodiment, the polypeptide acts as an active ingredient in the drug, further formulated with pharmaceutically acceptable additives.

In a further aspect, the present invention provides a method of preparing polypeptides set forth above, comprising the following step of:

performing polypeptide synthesis in accordance with the above-described amino acid sequence on a polypeptide synthesizer.

The present invention also provides another method of preparing polypeptides set forth above, comprising the following step of:

ligating the corresponding nucleotide sequence into a vector to form a recombinant vector;

transforming said recombinant vector into a host cell;

inducing said host cell to express said polypeptide; and separating said polypeptide.

In a preferred embodiment for the preparation method, the recombinant vector comprises a T7 promoter.

In a preferred embodiment for the preparation method, the vector is a plasmid, and the host cell is *E. coli.*

In a preferred embodiment for the preparation method, the plasmid is pIVEX2.3MCS, and the *E. coli.* strain is BL21.

By means of the aforementioned embodiments, it is contemplated in the present invention that a series of polypeptides are obtained by deleting any number of but at least one amino acid residues at any amino acid position in an orientation from the first amino acid residue at the N-terminal of the amino acid sequence shown in SEQ ID NO: 1 toward C-terminus thereof, that is, gradual subtraction of the N-terminal amino acid residues until deletion of 43 amino acid residues while preserving only 12 amino acid residues from the C-terminal of the sequence. Based this inventive concept, the gene for and the molecular structure of the pantapentacontapeptide were optimized, the length of the pantapentacontapeptide was successfully shortened by 78.2% while preserving and increasing its activities, and the polypeptides of interest were successfully synthesized with 99.2% purity by use of advanced peptide synthesis techniques, with all key parameters for industrialization acquired.

The present invention also succeeded in producing the polypeptide of interest through genetic engineering procedures. As the full length of the gene for the pantapentacontapeptide is only 165 bp, and approximately 180 bp upon addition of restriction enzyme sites, we chose the procedure that two parts of the gene (consisting of 4 fragments) were separately synthesized and then sequentially cloned into an expression vector. An expression plasmid pIVEX2.3MCS2-pantapentacontapeptide was constructed, which comprised the full-length gene for the pantapentacontapeptide under the control of the T7 promoter. This allowed the expression plasmid to successfully express the pantapentacontapeptide in a prokaryotic expression system with the T7 promoter.

The present invention has assessed more systemically the pharmacodynamics of the polypeptide of interest to be significantly effective, using the techniques such as light microscopy, electron microscopy, direct weighing, color B-type ultrasonic, etc. It was shown in the investigation that the polypeptide of interest has a good prophylaxic effectiveness on in vitro model of cardiocyte hypertrophy induced by various factors such as angiotensin II, NE, etc; exerts a very good suppression effect on the change in the MAPK activity stimulated by angiotensin II, etc; has a good therapeutic effect both on myocardial hypertrophy in a normal mouse model of reversed coarctation of thoracic aort (TAC) by in vivo surgery and on myocardial hypertrophy caused by acute volume overload (AVO) in normal rat; has also apparent effects of reversing myocardial remodeling, reversing pachynsis of vessel wall and lowering blood pressure in spontaneous hypertension rat (SHR).

It is demonstrated by preliminary safety assessment that the polypeptide of interest is extremely safe in administration. ① Cytotoxicity test: no cytotoxity (negtive); ② Genetic toxictiy test: no genetic cytotoxity (negtive);③ Mutagenicity test (Ames test): no mutagenic effect (negative). The tolerance dose of the polypeptide of interest in a mouse is greater than at least 50 mg/kg, the ratio of the tolerance dose to the effective dose is greater than at least 500; whereas the ratio of mouse $LD_{50}$/routine dosage (the clinical dosage is converted into the dosage in the mouse) of captopril, losartan and nifedipine, the typical hypotensive drugs with an effect of reversing myocardial hypertrophy, is 388, 349 and 157, respectively, indicating that the safety of the polypeptide of interest is significantly higher than that of the above drugs. Furthermore, No other toxic side-effects were observed during the course of the test.

EXAMPLE

Figure 1:
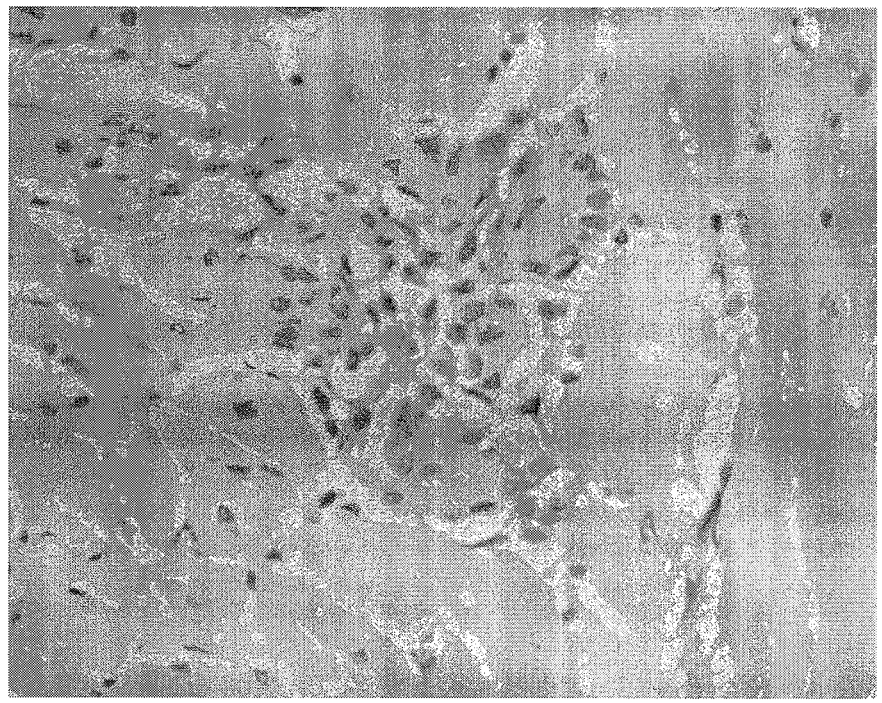
FIG. 1. Changes in morphology of cardiac muscle tissues from the SHR model group.

The invention is illustrated in greater details according to the specific embodiment of the present invention in combination with the drawings.

Example 1

Solid Phase Synthesis of the Polypeptide

1. Synthesis and Purification Processes for the Heptacosapeptide 25 g of resin (with the substituent constant of 0.6 mmol/g) was fed at pilot scale in the following steps. 1 kg of resin was used at manufacture scale, the feed quantity was enlarged proportionally, and the reaction time was extended.

1.1 Synthesis Process for the Heptacosapeptide 1. 25 g of Fmoc-Val-Wang resin was weighed precisely and placed into a 1000 ml reactor, followed by addition thereinto of DCM, shaken and soaked for 30 min, washed respectively with 500 ml of each of DCM, MeOH, and DMF two times, and subjected to sucking filtration to remove the solvent.

2. 500 ml of 20% piperidin/DMF was added, shaken at room temperature, and reacted for 30 min to remove the N-terminal Fmoc protective group. After the solvent was removed by sucking filtration, the resin was further washed with 500 ml of each of DCM, MeOH, and DMF two times, and the solvent was removed by sucking filtration.

3. 21.2 g of Fmoc-Leu-OH and 22.8 g of HBTU were weighed and dissolved in 500 ml of DMF, followed by addition thereinto of 40 ml of DIEA, and reacted at room temperature for 30 min with stirring. Then, the mixture was transferred into the reactor and reacted at room temperature for 2 h while shaking. After the reaction liquid was removed by sucking filtration, the resin was further washed with 500 ml of each of DCM, MeOH, and DMF two times, and the solvent was removed by sucking filtration.

4. Steps 2 and 3 were repeated, and all other conditions were kept unchanged and the steps were identical, except that the amino acid added in Step 3 was 35.8 g of Fmoc-Asn(Trt)-OH and the reaction time lasted 3 h.

5. Steps 2 and 3 were repeated, and all other conditions were unchanged and the steps were identical, except that the amino acid added in Step 3 was 27.6 g of Fmoc-Tyr(tBu)-OH.

6. Steps 2 and 3 were repeated, and all of other conditions were unchanged and the steps were identical, except that the amino acid added in Step 3 was 25.5 g of Fmoc-Glu(OtBu)-OH.

7. Steps 2 and 3 were repeated, and all of other conditions were unchanged and the steps were identical, except that the amino acid added in Step 3 was 28.1 g of Fmoc-Lys(Boc)-OH.

8. Steps 2 and 3 were repeated, and all of other conditions were unchanged and the steps were identical, except that the amino acid added in Step 3 was 21.2 g of Fmoc-Leu-OH.

9. Steps 2 and 3 were repeated, and all of other conditions were unchanged and the steps were identical, except that the amino acid added in Step 3 was 35.8 g of Fmoc-Asn(Trt)-OH.

10. Steps 2 and 3 were repeated, and all of other conditions were unchanged and the steps were identical, except that the amino acid added in Step 3 was 21.2 g of Fmoc-Leu-OH.

11. Steps 2 and 3 were repeated, and all of other conditions were unchanged and the steps were identical, except that the amino acid added in Step 3 was 36.7 g of Fmoc-Gln(Trt)-OH.

12. Steps 2 and 3 were repeated, and all of other conditions were unchanged and the steps were identical, except that the amino acid added in Step 3 was 21.2 g of Fmoc-Leu-OH.

13. Steps 2 and 3 were repeated, and all of other conditions were unchanged and the steps were identical, except that the amino acid added in Step 3 was 21.2 g of Fmoc-Ile-OH.

14. Steps 2 and 3 were repeated, and all of other conditions were unchanged and the steps were identical, except that the amino acid added in Step 3 was 23.9 g of Fmoc-Thr(tBu)-OH.

15. Steps 2 and 3 were repeated, and all of other conditions were unchanged and the steps were identical, except that the amino acid added in Step 3 was 24.7 g of Fmoc-Asp(OtBu)-OH.

16. Steps 2 and 3 were repeated, and all of other conditions were unchanged and the steps were identical, except that the amino acid added in Step 3 was 28.1 g of Fmoc-Lys(Boc)-OH.

17. Steps 2 and 3 were repeated, and all of other conditions were unchanged and the steps were identical, except that the amino acid added in Step 3 was 20.4 g of Fmoc-Val-OH.

18. Steps 2 and 3 were repeated, and all of other conditions were unchanged, and the steps were identical, except that the amino acid added in Step 3 was 19.8 g of Fmoc-Ala-OH.

19. Steps 2 and 3 were repeated, and all of other conditions were unchanged and the steps were identical, except that the amino acid added in Step 3 was 19.8 g of Fmoc-Ala-OH.

20. Steps 2 and 3 were repeated, and all of other conditions were unchanged and the steps were identical, except that the amino acid added in Step 3 was 23.2 g of Fmoc-Phe-OH.

21. Steps 2 and 3 were repeated, and all of other conditions were unchanged and the steps were identical, except that the amino acid added in Step 3 was 20.4 g of Fmoc-Val-OH.

22. Steps 2 and 3 were repeated, and all of other conditions were unchanged and the steps were identical, except that the amino acid added in Step 3 was 23.2 g of Fmoc-Phe-OH.

23. Steps 2 and 3 were repeated, and all of other conditions were unchanged and the steps were identical, except that the amino acid added in Step 3 was 39.0 g of Fmoc-Arg(pbf)-OH.

24. Steps 2 and 3 were repeated, and all of other conditions were unchanged and the steps were identical, except that the amino acid added in Step 3 was 21.2 g of Fmoc-Ile-OH.

25. Steps 2 and 3 were repeated, and all of other conditions were unchanged and the steps were identical, except that the amino acid added in Step 3 was 35.8 g of Fmoc-Asn(Trt)-OH.

26. Steps 2 and 3 were repeated, and all of other conditions were unchanged and the steps were identical, except that the amino acid added in Step 3 was 25.5 g of Fmoc-Glu(OtBu)-OH.

27. Steps 2 and 3 were repeated, and all of other conditions were unchanged and the steps were identical, except that the amino acid added in Step 3 was 23.9 g of Fmoc-Thr(tBu)-OH.

28. Steps 2 and 3 were repeated, and all of other conditions were unchanged and the steps were identical, except that the amino acid added in Step 3 was 24.7 g of Fmoc-Asp(OtBu)-OH.

29. 500 ml of 20% piperidin/DMF was added, shaken at room temperature, and reacted for 30 min to remove the N-terminal Fmoc protective group. After the solvent was removed by sucking filtration, the resin was further washed with 500 ml of each of DCM, MeOH, and DMF two times, and the solvent was removed by sucking filtration. The resin was vacuum-dried overnight.

30. The dried resin was weighed with total weight of 68 g, the weight increment being 43 g. The resin was transferred into a 250 ml round-bottomed flask, followed by adding thereinto 150 ml of TFA/TA/EDT/TIS/$H_2O$/phenol 7:1:1:0.1:0.35/0.5), and stirred at room temperature for 4 h. The resin was separated from the filtrate by sucking filtration, 2000 ml of ethyl ether at 0° C. was added into the filtrate, and the resulting precipitate was separated from ethyl ether by centrifugation and then dried to yield 40 g of the crude product of the heptacosapeptide.

1.2 Purification Process for the Heptacosapeptide 1.2.1 the lyophilized sample of the heptacosapeptide crude product was dissolved in DMSO, separated on a reverse-phase high performance liquid chromatography system and eluted via a gradient. The fractions of the main peak for the heptacosapeptide were collected, pooled and re-lyophilized to obtain the initially purified raw material of the heptacosapeptide. The lyophilized product post the initial purification was dissolved in 15% acetonitrile and subjected to the second purification on a reverse-phase high performance liquid chromatography system. The fractions of the main peak were collected with the contaminants near the main peak being removed, pooled and re-lyophilized to obtain the refined heptacosapeptide.

1.2.2 chromatography conditions were as follows:
Chromatography equipment: Varian Liquid Chromatography Equipment prepstar and its softerware for operation and analysis;
Chromatography column; the chromatography column $C_{18}$ (250×50 mm) filled with Load & Lock;
Mobile phase: A: 0.05% TFA/2% acetonitrile/water; B: 90% acetonitrile/water;
elution gradient: initial purification: 8-8-32-57% B mobile phase for total of 70 min, level gradient for 5 min;
The second purification: 0-0-34-55% B mobile phase for total of 70 min, level gradient for 5 min;
Flow rate: 50 ml/min;
Wavelength for UV-detection: 275 nm.

2. Synthesis and Purification Processes for the Pantapentacontapeptide 25 g of resin (with the substituent constant of 0.6 mmol/g) was feed at pilot scale in the following steps. 1 kg of resin was used at manufacture scale, the feed quantity was enlarged in proportion, and the reaction time was extended.

1. 25 g of Fmoc-Val-Wang resin was weighed precisely and placed into a 67.63 fl oz reactor, followed by addition thereinto of DCM, shaken and soaked for 30 min, washed respectively with 500 ml of each of DCM, MeOH, and DMF two times, and subjected to sucking filtration to remove the solvent.

2. 500 ml of 20% piperidin/DMF was added, agitated at room temperature, and reacted for 30 min to remove the N-terminal Fmoc protective group. After the solvent was removed by sucking filtration, the resin was further washed with 500 ml of each of DCM, MeOH, and DMF two times, and the solvent was removed by sucking filtration.

3. 21.2 g of Fmoc-Leu-OH and 22.8 g of HBTU were weighed and dissolved in 500 ml of DMF, followed by addition thereinto of 40 ml of DIEA, and reacted at room temperature for 30 min with stirring. Then, the mixture was transferred into the reactor and reacted at room temperature for 2 h while shaking. After the reaction liquid was removed by sucking filtration, the resin was further washed with 500 ml of each of DCM, MeOH, and DMF two times, and the solvent was removed by sucking filtration.

4. Washing and deprotection in Step 2 and 3 were repeated, and the amino acids were sequentially introduced until the last amino acid was reacted.

5. 750 ml of 20% piperidin/DMF was added, shaken at room temperature, and reacted for 30 min to remove the N-terminal Fmoc protective group. After the solvent was removed by sucking filtration, the resin was further washed with 500 ml of each of DCM, MeOH, and DMF two times, and the solvent was removed by sucking filtration. The resin was vacuum-dried overnight.

6. The dried resin was weighed with total weight of 113 g, the weight increment being 88 g. The resin was transferred into a 250 ml round-bottomed flask, followed by adding thereinto 8.45 fl oz of TFA/TA/EDT/TIS/$H_2$O/phenol 7:1:1:0.1:0.35/0.5), and stirred at room temperature for 4 h. The resin was separated from the filtrate by sucking filtration, 3000 ml of ethyl ether at 0° C. was added into the filtrate, and the resulting precipitate was separated from the ethyl ether by centrifugation and then dried to yield 85 g of the crude product of the pantapentacontapeptide.

7. The Refining process and chromatography conditions were set with reference with those for the heptacosapeptide.

3. Synthesis and Purification Processes for the Dodecapeptide.

1-4. The same with the section above for the pantapentacontapeptide.

5. 500 ml of 20% piperidin/DMF was added, shaken at room temperature, and reacted for 30 min to remove the N-terminal Fmoc protective group. After the solvent was removed by sucking filtration, the resin was further washed with 500 ml of each of DCM, MeOH, and DMF two times, and the solvent was removed by sucking filtration. The resin was vacuum-dried overnight.

6. The dried resin was weighed with total weight of 46 g, the weight increment being 21 g. The resin was transferred into a 250 ml round-bottomed flask, followed by adding thereinto 100 ml of TFA/TA/EDT/TIS/$H_2$O 7:1:1:0.1:0.35), and stirred at room temperature for 3 h. The resin was separated from the filtrate by sucking filtration, 1500 ml of ethyl ether at 0° C. was added into the filtrate, and the resulting precipitate was separated from the ethyl ether by centrifugation and then dried to yield 0.67 oz of the crude product of the dodecapeptide.

7. The refining process and chromatography conditions were set with reference with those for the heptacosapeptide.

Example 2

Expression of Pantapentacontapeptide and Heptacosapeptide by Genetic Engineering and Purification Thereof Based on the nucleotide sequences for the pantapentacontapeptide and the heptacosapeptide, the corresponding oligonucleotide sequences were designed to construct the expression vector for the peptide.

For the pantapentacontapeptide, four single-stranded oligonucleotides were synthesized as follows:

```
55-1: 60 bp
5' tcgagctccatgggtcgagaattcattctgaagatgttcgtcgactaaacgttctctgca 3' (SEQ ID NO: 21)

55-2: 52 bp
5' gagaacgtttagtcgacgaacatcttcagaatgaattctcgacccatggagc 3' (SEQ ID NO: 22)

55-3: 85 bp
5' gaggtcgacctgaacccagacagtgacaaaattatctactcccacttcacgtgtgccacagac accgagaatatccgctttgtct 3' (SEQ ID NO: 23)

55-4: 85 bp
5' tagcccggggaccagattgtactccttcaggttcagctggaggatggtgtccttgacggctgc aaagacaaagcggatattctcg 3' (SEQ ID NO: 24)

For the heptacosapeptide, two single-stranded oligonucleotides were
synthesized as follows:
27-1:
5' catggacaccgagaatatccgctttgtctttgcagccgtcaaggacaccatcctccagctgaa cctgaaggagtacaatctggtctaaccc 3' (SEQ ID NO: 25)

27-2:
5' gggttagaccagattgtactccttcaggttcagctggaggatggtgtccttgacggctgcaaa gacaaagcggatattctcggtgtc 3' (SEQ ID NO: 26)
```

The first and second single-stranded oligonucleotides synthesized for the pantapentacontapeptide were annealed to form a double-stranded DNA fragment with cohesive ends, the resulting DNA fragment was unidirectionally cloned between the restriction sites Xho I and Pst I on the plasmid pEGFP-N1 (provided by Department of Genetics, Third Military Medical University, Chongqing, China), and the constructed plasmid was designated pEGFP-A. As there were 20 complementary bases at the 3' ends of the third and fourth synthesized single-stranded oligonucleotides, the third and fourth oligonucleotides were annealed and elongated by Taq polymerase to form a double-stranded DNA fragment B. the amplified fragment was observed at the 150 bp DNA molecular weight marker in 2.5% agrose gel electrophoresis. The fragment B was double-digested by Sal I and Sma I and then unidiretionally cloned between the restriction sites Sal I and Sma I on the plasmid pEGFP-A, and the constructed plasmid was designated pEGFP-55, which comprises the whole pantapentacontapeptide gene. The pantapentacontapeptide gene was cleaved out by double digestion with Xho I and Sma I and inserted between the restriction sites Xho I and Sma I on the plasmid pIVEX2.3-MCS, and the constructed plasmid was designated pIVEX2.3MCS-55. The screening for the plasmid of interest can be performed as follows: the candidate plasmid was double-digested with Xho I and Sma I, analyzed by 2.5% agrose gel electrophoresis, and identified as a positive clone if there was a band approximately at the 180 bp DNA molecular weight marker.

The first and second single-stranded oligonucleotides synthesized for the heptacosapeptide were annealed to directly form a double-stranded DNA fragment with cohesive ends for Nco I and Sma I, the pIVEX2.3 plasmid was double-digested with Nco I and Sma I and electrophorosised, and then the plasmid fragment with cohesive ends was recovered by a gel recovery kit. The heptacosapeptide gene was unidiretionally cloned into the plasmid pIVEX2.3 (purchased from Roche company, Switzerland) with T4 DNA ligase. The positive clone comprises the heptacosapeptide gene and is designated pIVEX2.3-27. Six colonies with the ligated recombinant plasmid on a plate containing ampicillin were picked into 5 ml of LB medium and cultured overnight; the plasmid was extracted, double-digested with Nco I and Sma I and electrophorosised for identification; the clone identified as positive was further confirmed by sequencing. It was established that pIVEX2.3MCS-55 and pIVEX2.3-27 were successfully constructed. pIVEX2.3MCS-55 and pIVEX2.3-27 were individually transformed into BL21 (DE3) pLysE competent cells (purchased from Sangon Biotech (Shanghai) Co., Ltd.), the plasmid was extracted from the transformed colony with a plasmid extraction kit and identified by restriction digestion, and a single colony was picked and cultured with shaking at 37° C., 180 rpm/min in 2 ml of a LB medium containing ampicillin (100 µg/ml) for 10 h. 200 µl of the above bacterial suspension was added into 250 ml of an ampicillin-containing LB medium, cultured with shaking at 37° C., 180 rpm/min for 10 h, followed by adding IPTG to its final concentration of 1 mmol/L, cultured further at 37° C. for 4-6 h and then at 30° C. for 10 h. The bacterial cells were collected by centrifugation and stored at −70° C. until using. 1 g wet weight of the collected bacteria was resuspended with 5 ml of the binding buffer, disrupted by ultrasonicaton (setting: plus for 6 s, amplitude of 15-20, disruption on ice for 8-10 min), and centrifuged at 12000 rpm/min for 10 min, The supernatant was pipetted for purification. Purification was performed by nickel-chelate affinity chromatography under denaturing condition: a Ni-column was equilibrated first with 5 ml of a denaturing binding buffer. The supernatant originating from ultrasonication was allowed to pass through the column with a controlled flow rate of no more than 10 m per hour, and an eluate was collected. The column was eluted with 5 ml of a denaturing washing buffer A, and the eluate was collected. 1 ml of a liquid was formulated with the non-denaturing washing buffer B and the denaturing washing buffer B in the ratio 0:1, 1:9, 2:8, 3:7, 4:6, 5:5, 6:4, 7:3, 8:2, 9:1, and 1:0. The column was eluted with the above-described liquids and then with 2 ml of the non-denaturing washing buffer B, the whole course should be no less than 2-3 h, and the eluate was collected. 3 ml of the elution buffer A was allowed to pass through the column to elute the protein, and the eluate was collected. 2×3 ml of the elution buffer A was allowed to pass through the column to elute the protein, and the eluate was collected. The purity of the protein was identified by SDS-PAGE. It was shown that the BL21 (DE3) bacteria expresses the polypeptide of interest, the quantity of expression in the polypeptide of interest amounts to about 10% of total protein of bacterial cells, and the yield is about 1.5 mg of the polypeptide of interest purified from 250 ml of bacterial suspension after Ni-column purification and renaturation. Most of the polypeptide of interest was eluted with 500 mmol/L imidazole and produced a single band in SDS-PAGE, with purity of above 98% as determined by densitometry.

Example 3

A Serial of the Polypeptides of the Present Invention is Able to Reduce the Protein Content in Model of Rat Cardiocyte Hypertrophy Induced by Norepinephrine 1. Wistar rats 1-3 day postpartum (purchased from Center for Experimental Animal, Third Military Medical University) was used, sacrificed by cervical dislocation, and fixed on a dissecting table. The ventral skin of the corpus was disinfected with 2% iodine tincture and then 75% ethanol. The heart was removed, cutted into pieces of about 1-3 mm$^3$, digested repeatedly with a digestion solution containing 0.08% trypase, 0.02% EDTA, and 0.05% collogen. The cells were collected in DMEM containing 10% fetal bovine serum and cultured in an incubator at 37° C., 5% $CO_2$.

2. The cardiocytes cultured for 48 h were subjected to replacement of the DMEM with a serum-free DMEM culture media and further cultured for 24 h before addition of a drug according to the following groups:

Normal control group; 10 µl of PBS was added.
  Norepinephrine group; norepinephrine (NE, Serva Corporation, USA) was added at 1 µmol/L.
  Polypeptide-dosed group: NE was added, while the corresponding polypeptide drug was added at 10 nmol/L.

3. After addition of the drug, the cells were further cultured for 24 h and then the culture media was discarded. The culture was washed with PBS, followed by adding 0.5 ml of 5% trichloracetic acid per well, and left at 4° C. for 1 h. The precipitate was dissolved in 1 ml of 0.1 mol/L NaOH. The protein content was determined by Lowry method.

4. Result: each of the pantapentacontapeptide, pentatetracontapeptide, pentatriacontapeptide, triacontapeptide, heptacosapeptide, pentadicosapeptide, dicosapeptide, heptadecapeptide, and pentadecapeptide at 10 nmol/L is able to significantly decrease the protein content in the hypertrophic cardiocyte induced by NE, and the dodecapeptide has no manifest effect (as shown in Table 1).

TABLE 1

Effect of a serial of polypeptides of the present invention on the protein content in the cultured cardiocytes of the rats (n = 6, $\bar{x} \pm s$)

| Group | Dosage (nmol/L) | Protein content ($\mu g/10^5$ cells) |
|---|---|---|
| Control | — | 80.5 ± 13.9 |
| NE | 1000 | 121.0 ± 13.2** |
| Pantapentacontapeptide | 10 | 90.3 ± 10.8## |
| Pentatetracontapeptide | 10 | 92.7 ± 12.3## |
| Pentatriacontapeptide | 10 | 93.4 ± 12.0## |
| Triacontapeptide | 10 | 99.8 ± 9.9## |
| Heptacosapeptide | 10 | 89.4 ± 10.7## |
| Pentadicosapeptide | 10 | 100.2 ± 11.6## |
| Dicosapeptide | 10 | 103.4 ± 11.4# |
| Heptadecapeptide | 10 | 96.4 ± 10.5## |
| Pentadecapeptide | 10 | 104.3 ± 12.6## |
| Dodecapeptide | 10 | 113.3 ± 11.6 |

**P < 0.01 vs control group;
P < 0.05,
P < 0.01 vs NE group.

Example 4

A Serial of the Polypeptides of the Present Invention is Able to Reduce the Protein Content in Model of Rat Cardiocyte Hypertrophy Induced by Angiotensin II (Ang II)

1. The cardiocytes were cultured for 48 h in the same way as described above, then subjected to replacement of the DMEM with a serum-free DMEM culture media, and further cultured for 24 h before addition of a drug according to the following groups: normal control group: 10 μl of PBS was added; Ang II group; Ang II was added at 1 μmol/L; serial polypeptide-dosed group: Ang II was added, while each of the dodecapeptide, pentadecapeptide, heptacosapeptide, pantapentacontapeptide was added at 10 nmol/L.

2. After addition of the drug, the cells were further cultured for 24 h and then the culture media was discarded. The culture was washed with PBS, followed by adding 0.5 ml of 5% trichloracetic acid per well, and left at 4° C. for 1 h. The precipitate was dissolved in 1 ml of 0.1 mol/L NaOH. The protein content was determined by Lowry method.

3. Result: Addition of Ang II into the cell culture media is able to significantly increase the protein content in the cardiocyte (μg: 143.2±5.49 vs 113.9±7.48, p<0.01) as compared to the normal control group. In comparison with Ang II, the pentadecapeptide, heptacosapeptide, and pantapentacontapeptide can decrease the protein content in the cardiocyte in varying degrees, whereas the dodecapeptide has no manifest effect (seen in Table 2).

TABLE 2

Effect of the serial polypeptides on the protein content in the hypertrophic cardiocyte induced by angiotensin II (n = 6, $\bar{x} \pm s$)

| Group | Dosage (nmol/L) | Protein content ($\mu g/10^5$ cells) |
|---|---|---|
| Control | — | 113.9 ± 7.48 |
| Ang II | 1000 | 143.2 ± 5.49** |
| Dodecapeptide | 10 | 144.0 ± 11.7 |
| Pentadecapeptide | 10 | 130.6 ± 10.79# |
| Heptacosapeptide | 10 | 125.3 ± 9.41## |
| Pantapentacontapeptide | 10 | 127.2 ± 6.33## |

Note:
**P < 0.01 vs control group;
P < 0.05,
P < 0.01 vs Ang II group.

Example 5

Polypeptides Able to Significantly Suppressing Myocardial Hypertrophy in Mice Induced by Norepinephrine Fifty of the mice used in the experiment (purchased from Center for Experimental Animals, Third Military Medical University) was assigned into five groups with 10 mice per group. The mice in the control group were administrated with 0.1% ascorbic acid-3 mg % potassium sodium tartrate-physiological saline, The mice in the model group were administrated with 0.1% ascorbic acid-6 mg % norepinephrine bitartrate-physiological saline (equivalent to 1.5 mg/kg NE); The mice in three dosing groups were administrated with the pentadecapeptide, the heptacosapeptide, and the pantapentacontapeptide at 30 μg/kg respectively, while administration of 0.1% ascorbic acid—6 mg % norepinephrine bitartrate—physiological saline. The administration was performed consecutively by intraperitoneal injection (ip), twice a day (bid), for 15 days. The dosing volumes for each group were 50 ml/kg. Then, the animals were sacrificed by cervical dislocation. The heart was removed by thoracotomy, washed with the chilled physiological saline to get rid of blood stain, blotted with filter paper, weighed on a scale. The atriums and the right ventricle were carefully removed (with the interventricular septum left), and the left ventricle was weighed.

The result shows that the serial polypeptides can significantly prevent the occurrence of myocardial hypertrophy in the mice, and various indicators about myocardial hypertrophy in all other groups are significantly improved, except for the heart weight in the pentadecapeptide group (which decreases by 9.9%, while P>0.05) (seen in Table 3).

TABLE 3

Effect of the serial polypeptides on the myocardial hypertrophy in the mice ($\bar{x} \pm s$)

| Group | N | BW(g) | HW(mg) | LVW(mg) | HI(mg/g) | LVI(mg/g) |
|---|---|---|---|---|---|---|
| Control | 10 | 25.1 ± 2.19 | 98.8 ± 9.68 | 70.8 ± 8.21 | 3.95 ± 0.31 | 2.82 ± 0.27 |
| NE | 8 | 23.2 ± 1.69 | 112.1 ± 12.1* | 85.6 ± 9.16** | 4.82 ± 0.44** | 3.69 ± 0.36** |
| Pentadecapeptide | 9 | 23.6 ± 2.51 | 100.9 ± 12.8 | 74.7 ± 9.25## | 4.27 ± 0.42## | 3.16 ± 0.39## |
| Heptacosapeptide | 8 | 23.1 ± 2.26 | 95.2 ± 5.79# | 67.9 ± 6.30## | 4.17 ± 0.52## | 2.98 ± 0.48## |
| Pantapentacontapeptide | 8 | 23.3 ± 2.05 | 99.0 ± 16.3# | 72.9 ± 12.8## | 4.24 ± 0.59## | 3.13 ± 0.50## |

Note:
BW—body weight; HW—heart weight; LVW—left ventricular weight; HI—heart index; LVI—left ventricular index or myocardial hypertrophy index.
*P < 0.05,
**P < 0.01 vs control group;
P < 0.05,
P < 0.01 vs NE group

Example 6

The Present Invention a Serial of Polypeptide Significantly Suppress the Myocardial Hypertrophy in Rats Induced by Norepinephrine Thirty of Wistar rats were selected and assigned into five groups with 6 rats per group. The rats in the control group were administrated with 0.1% ascorbic acid-3 mg % potassium sodium tartrate-physiological saline; the rats in the model group were administrated with 0.1% ascorbic acid-6 mg % norepinephrine bitartrate-physiological saline; the rats in the three dosing groups were administrated with the pentadecapeptide, the heptacosapeptide, and the pantapentacontapeptide at 15 µg/kg respectively, while administration of norepinephrine. The dosing volume for each group was 33 ml/kg, and the administration was performed consecutively by ip, bid, for 20 days. At that time, the heart and left ventricle were weighed.

The result shows that the pentadecapeptide can significantly decrease the left ventricular index, the heptacosapeptide and the pantapentacontapeptide can significantly decrease the left ventricular weight, the heart index and the left ventricular index (seen in Table 4).

operation group, operation model group (SRS), and polypeptide-dosing group. Before the operation, animals were fasted overnight and given Ad libitum access to water, and then anesthetized with pentobarbital sodium and underwent celiotomy. The abdominal aorta was separated, and a 8 G needle (0.80 mm outer diameter) was fastened along the abdominal aorta above the right renal artery with a silk suture before the needle was quickly removed. Then, the abdomen was closed by suturation. The rats in the sham operation group were subjected to the same treatment as the aforementioned, except no ligation with silk suture. From the first day post operation, the rats in the sham operation control group and in the operation model group were administrated with physiological saline at 7.5 ml/kg, ip, once a day; the rats in the dosing group were administrated with the pentadecapeptide, heptacosapeptide, and pantapentacontapeptide at 15 µg/kg respectively, ip, once a day. Rats were reared routinely for 3 weeks and then sacrificed. The heart was removed by thoracotomy, washed with the chilled physiological saline to get rid of blood stain, blotted with filter paper. The heart and the left ventricle were weighed on a scale.

The result demonstrates that the serial polypeptides can significantly prevent the occurrence of myocardial hypertrophy in the rats, and there are significant decreases in HW, LVW, HI, and LVI (seen in Table 5).

TABLE 4

Effect of the serial polypeptides on myocardial hypertrophy in the rats induced by norepinephrine (n = 6, $\bar{x} \pm s$)

| Group | BW (g) | HW (g) | LVW (g) | HI (g/kg) | LVI (g/kg) |
|---|---|---|---|---|---|
| Control | 189 ± 15 | 0.573 ± 0.035 | 0.408 ± 0.027 | 3.043 ± 0.178 | 2.166 ± 0.114 |
| NE | 187 ± 5.0 | 0.690 ± 0.078* | 0.555 ± 0.055** | 3.674 ± 0.348** | 2.954 ± 0.225** |
| Pentadecapeptide | 188 ± 12 | 0.673 ± 0.055 | 0.490 ± 0.038 | 3.580 ± 0.226 | 2.606 ± 0.154[#] |
| Heptacosapeptide | 200 ± 13 | 0.622 ± 0.032 | 0.442 ± 0.017[##] | 3.111 ± 0.041[##] | 2.213 ± 0.056[##] |
| Pantapentacontapeptide | 190 ± 21 | 0.630 ± 0.052 | 0.450 ± 0.036[##] | 3.310 ± 0.137[#] | 2.368 ± 0.166[##] |

Note:
BW—body weight;
HW—heart weight;
LVW—left ventricular weight;
HI—heart index;
LVI—left ventricular index or myocardial hypertrophy index.
*$P < 0.05$,
**$P < 0.01$ vs control group;
[#]$P < 0.05$,
[##]$P < 0.01$ vs NE group

Example 7

Polypeptides that Significantly Prevent Myocardial Hypertrophy in Rats Induced by Aortic Coarctation Healthy male Wistar rats (purchased from Center for Experimental Animals, Third Military Medical University) were randomly assigned into the following groups: the sham-

TABLE 5

Effect of the serial polypeptides on the myocardial hypertrophy in rats induced by aortic coarctation ($\bar{x} \pm SEM$)

| | n | BW(g) | HW(mg) | LVW(mg) | HI(mg/g) | LVI(mg/g) |
|---|---|---|---|---|---|---|
| Sham-operation | 6 | 222 ± 8.2 | 713 ± 23.3 | 399 ± 24.9 | 3.22 ± 0.08 | 1.80 ± 0.07 |
| SRS | 5 | 204 ± 5.8 | 813 ± 31.3* | 508 ± 26.4* | 3.98 ± 0.09** | 2.48 ± 0.10** |
| Pentadecapeptide | 5 | 208 ± 5.6 | 706 ± 30.8[#] | 418 ± 12.3[#] | 3.39 ± 0.10[##] | 2.01 ± 0.06[##] |
| Heptacosapeptide | 5 | 211 ± 6.4 | 696 ± 30.7[##] | 413 ± 22.1[#] | 3.30 ± 0.08[##] | 1.96 ± 0.08[##] |
| Pantapentacontapeptide | 5 | 215 ± 8.0 | 702 ± 31.3[##] | 409 ± 24.6[#] | 3.27 ± 0.08[##] | 1.90 ± 0.07[##] |

[##]$P < 0.01$ vs SRS group.
**$P < 0.01$ vs sham-operation group;
[#]$P < 0.05$,

Example 8

The Serial Polypeptides of the Present Invention can Prevent Myocardial Remodeling in Rats with Spontaneous Hypertension 1. Thirty 13-week-old rats with spontaneous hypertension (SHR, purchased from Beijing Vital River Laboratory Animal Technology Co. Ltd., Beijing) were selected and randomly assigned into five groups with 6 rats per group:

SHR model group (Vehicle): 0.9% physiological saline, intraperitoneal injection at a dosage of 5 ml/kg, bid.

Positive control group (losartan): potassium losartan at a dosage of 6 mg/kg, intragastric administration, qd.

The pentadecapeptide group: administration of the pentadecapeptide at a dosage of 30 μg/kg by intraperitoneal injection, bid.

The heptacosapeptide group: administration of the heptacosapeptide at a dosage of 30 μg/kg by intraperitoneal injection, bid.

The pantapentacontapeptide group: administration of the pantapentacontapeptide at a dosage of 30 μg/kg by intraperitoneal injection, bid.

Six of INKY (Wistar-Kyoto) rats (purchased from Center for Experimental Animals, Third Military Medical University) were additionally selected as the normal control.

2. Intervention with the drug was performed consecutively for eight weeks (from Week 14 to Week 21). The body weights of all the tested rats were obtained once every two weeks, and the administration dosage was adjusted based on body weights.

3. The result suggests:

(1) the serial polypeptides have some hypotensive effect and can significantly decrease the systolic blood pressure of artery in the SHR (seen in Table 6).

TABLE 6

Effect the serial polypeptides of the present invention on the systolic blood pressure in SHRs ($\bar{x} \pm s$, n = 6).

| Group | Dosage | Systolic blood pressure of artery (mmHg) | | | | |
|---|---|---|---|---|---|---|
| | | 0 w | 2 w | 4 w | 6 w | 8 w |
| WKY | — | 143.8 ± 10.79 | 144.8 ± 9.03 | 143.8 ± 8.16 | 144.4 ± 9.67 | 142.6 ± 4.82 |
| Vehicle | — | 176.9 ± 1.82 | 207.4 ± 8.80## | 225.3 ± 16.24## | 238.6 ± 8.09* | 248.1 ± 7.27* |
| Losartan | 6 mg/kg | 178.3 ± 2.24 | 165.1 ± 4.80** | 177.1 ± 8.27** | 178.3 ± 6.23** | 172.6 ± 4.82** |
| Pentadecapeptide | 30 μg/kg | 177.3 ± 6.42 | 190.4 ± 7.75** | 200.2 ± 4.13** | 217.1 ± 8.82** | 224.1 ± 6.37** |
| Heptacosapeptide | 30 μg/kg | 180.0 ± 3.60 | 185.2 ± 6.92** | 189.4 ± 6.34** | 211.6 ± 3.97** | 202.3 ± 3.87** |
| Pantapentacontapeptide | 30 μg/kg | 178.2 ± 4.15 | 189.8 ± 7.80** | 193.4 ± 5.31** | 216.0 ± 5.55** | 218.3 ± 8.54** |

P < 0.01 vs WKY;
**P < 0.01 vs Vehicle (2) the serial polypeptides of the present invention can significantly improve myocardial remodeling in the SHRs, and can significantly lead to decrease in HW, LVW, HI and LVI in the rats (Table 7) as well as in left ventricular posterior wall thickness (PWT) and intervertricular septum thickness (IVST) in the SHRs (Table 8).

TABLE 7

Effect of the serial polypeptides on the myocardial hypertrophy in the rats ($\bar{x} \pm s$, n = 6).

| Group | Dosage | BW (g) | HW(mg) | LVW(mg) | HI(mg/g) | LVI(mg/g) |
|---|---|---|---|---|---|---|
| WKY | — | 300 ± 8 | 876 ± 29 | 582 ± 20 | 2.92 ± 0.05 | 1.94 ± 0.10 |
| Vehicle | — | 309 ± 6 | 1176 ± 39## | 950 ± 31## | 3.80 ± 0.08## | 3.07 ± 0.13## |
| Losartan | 6 mg/kg | 288 ± 9 | 1003 ± 16** | 789 ± 88 | 3.48 ± 0.05** | 2.74 ± 0.28 |
| Pentadecapeptide | 30 μg/kg | 307 ± 8 | 1055 ± 30** | 775 ± 28** | 3.44 ± 0.05** | 2.46 ± 0.04** |
| Heptacosapeptide | 30 μg/kg | 304 ± 10 | 849 ± 23** | 609 ± 99** | 2.80 ± 0.03** | 2.01 ± 0.07** |
| Pantapentacontapeptide | 30 μg/kg | 291 ± 7 | 949 ± 28** | 705 ± 49** | 3.26 ± 0.05** | 2.30 ± 0.08** |

Note:
**P < 0.01 vs Vehicle;
P < 0.01 vs WKY

TABLE 8

Effect of the polypeptides of the present invention on the echocardiographic parameters in SHRs ($\bar{x} \pm s$, n = 6).

| Group | Dosage | PWT (mm) | IVST (mm) | LAD (mm) | LVEDD (mm) | LVESD (mm) | EF (%) | FS (%) | SV (ml) |
|---|---|---|---|---|---|---|---|---|---|
| WKY | — | 1.75 ± 0.19 | 1.45 ± 0.26 | 3.43 ± 0.12 | 5.41 ± 0.32 | 2.42 ± 0.24 | 90.1 ± 3.13 | 55.2 ± 3.99 | 0.35 ± 0.05 |
| Vehicle | — | 2.88 ± 0.21## | 2.22 ± 0.17## | 3.33 ± 0.26 | 5.28 ± 0.58 | 2.39 ± 0.32 | 89.1 ± 3.04 | 54.7 ± 3.06 | 0.30 ± 0.09 |
| Losartan | 6 mg/kg | 2.25 ± 0.21* | 1.87 ± 0.18* | 3.25 ± 0.23 | 5.05 ± 0.42 | 2.33 ± 0.18 | 88.8 ± 2.62 | 53.6 ± 3.57 | 0.21 ± 0.04 |
| Pentadecapeptide | 30 μg/kg | 1.96 ± 0.16** | 1.62 ± 0.20** | 3.39 ± 0.33 | 5.38 ± 0.31 | 2.41 ± 0.35 | 89.4 ± 3.90 | 55.1 ± 4.33 | 0.32 ± 0.05 |
| Heptacosapeptide | 30 μg/kg | 1.85 ± 0.19** | 1.30 ± 0.24** | 3.45 ± 0.49 | 5.35 ± 0.40 | 2.40 ± 0.21 | 90.0 ± 1.26 | 55.1 ± 1.56 | 0.34 ± 0.06 |

TABLE 8-continued

Effect of the polypeptides of the present invention on the echocardiographic parameters in SHRs ($\bar{x} \pm s$, n = 6).

| Group | Dosage | PWT (mm) | IVST (mm) | LAD (mm) | LVEDD (mm) | LVESD (mm) | EF (%) | FS (%) | SV (ml) |
|---|---|---|---|---|---|---|---|---|---|
| Pantapenta-contapeptide | 30 µg/kg | 1.93 ± 0.31** | 1.44 ± 0.17** | 3.45 ± 0.37 | 5.23 ± 0.37 | 2.23 ± 0.25 | 90.5 ± 2.41 | 57.6 ± 4.37 | 0.30 ± 0.10 |

Note:
P < 0.01 vs WKY;
*P < 0.05,
**P < 0.01 vs Vehicle
LAD: left atrium sinistrum diameter; LVEDD: left ventricular end diastolic diameter; EF: ejection fraction; FS: shortening fraction; SV: stroke volume.

(3) Effect of serial polypeptides of the present invention on morphology of the cardiac muscle tissues in the SHRs:

Morphological analysis suggests: while the trans diameter (TDM) and the cross section area (CSA) of the cardiocyte in rats from model group are significantly increased in comparison with those in the WKY group (P<0.01), the CSA of the rats in the group dosed with the serial polypeptides and in the losartan group is significantly decreased in comparison with those in the model group significant (P<0.01) (seen in Table 9).

TABLE 9

Morphologica analyasis on rat cardiocytes ($\bar{x} \pm s$, n = 6)

| Group | Dosage | TDM (µm) | CSA (µm$^2$) |
|---|---|---|---|
| WKY | — | 11.30 ± 2.35 | 248 ± 26 |
| Vehicle | — | 15.56 ± 2.94## | 375 ± 11## |
| Losartan | 6 mg/kg | 13.83 ± 2.54 | 335 ± 20** |
| Pentadecapeptide | 30 µg/kg | 14.88 ± 2.56 | 329 ± 24** |
| Heptacosapeptide | 30 µg/kg | 12.33 ± 1.84** | 286 ± 22** |
| Pantapentacontapeptide | 30 µg/kg | 14.62 ± 2.36 | 313 ± 29** | p < 0.01 vs WKY;
**p < 0.01,
**p < 0.01 vs vehicle.

It was seen under the light microscope that the cardiocyte nucleus was blue, cellular plasma was pink, and the collogen was not stained.

In SHR model group (FIG. 1): myocardial fibers become thicken, swollen, have unclear interspaces, broken, fused or disorderly arranged, and part of the myocardial fibers show more distinct hydropic degeneration of the myocardium in large area; cardiocytes show significant hypertrophy, cloudy swelling, vacular-like degeneration; the cellular nucleuses are enlarged or undergo pyknosis; the cellular content become granular, broken, and fused, even necrosis is present; spotted necrotic foci and focal necrotic foci are seen under a few views; vessel walls become thicken; smooth muscle cells proliferate and hypertrophy; interstitial myocardial fibrosis are observed under individual views. But generally speaking, the degree of fibrosis is relatively mild and inflammatory response is relatively severe in the model group; necrotic foci are observed under a few views.

Figure 2:
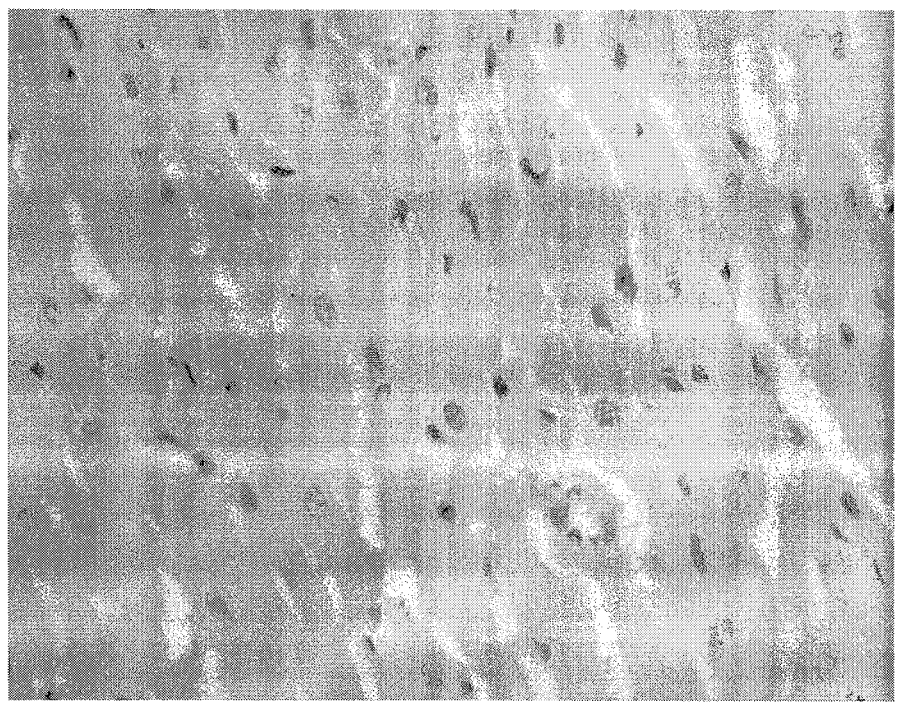
FIG. 2. Changes in morphology of cardiac muscle tissues from the losartan group.

In the losartan group (FIG. 2): Pathological changes are somewhat improved and presented predominantly as infiltration of the inflammatory cells. It can be seen that the cardiocytes show inflammatory changes, such as, apparent cloudy swelling, hypertrophy, etc, and necrotic foci are still observed under a few views.

Figure 3:
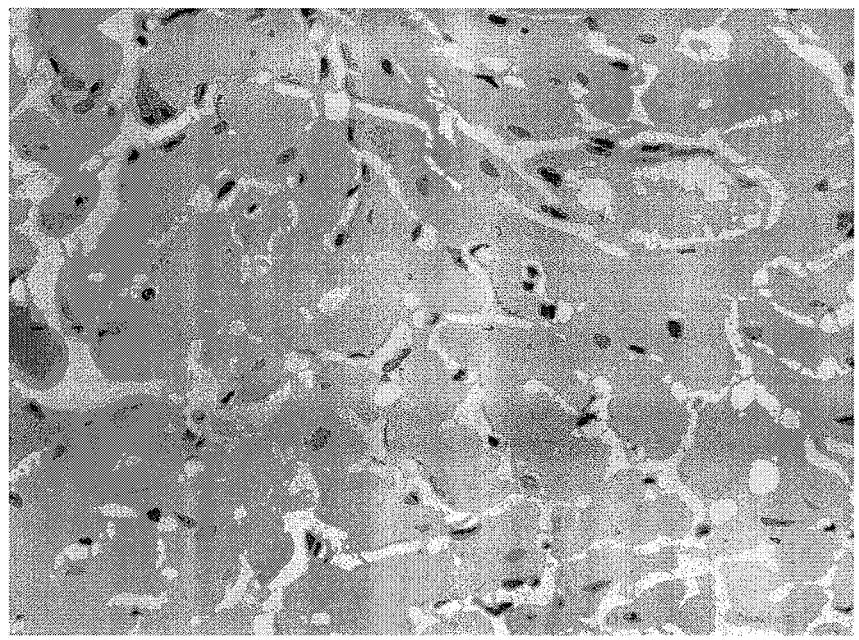
FIG. 3. Changes in morphology of cardiac muscle tissues from the heptacosapeptide group.

In the heptacosapeptide group (FIG. 3): As compared to the SHR model group, the above-described pathological changes in cardiocytes are significantly alleviated. Improvement of the pathological changes in the heptacosapeptide group is essentially approximate to the status in the normal control group, and inflammatory changes are seen occasionally under individual views, such as, mild swelling of cardiocytes, etc. No necrotic foci are formed, and morphologies of the myocardial fibers and vessel walls keep normal.

Figure 4:
FIG. 4. Changes in ultramcirostructure of cardiac muscle tissues from the SHR model group.

(4) Effect of the heptacosapeptide on the ultrastructure of the SHR cardiocyte (PHILIPS-TECNI10 Transmission electron microscope, Holland):

In SHR model group (FIG. 4): the volume of the cardiocyte is enlarged, its nuclear membrane is incomplete, its nucleus presents irregular changes such as hypertrophy, deformation, lysis, etc; the sarcoplasmic reticulum is dilated; the mitochondria proliferate, are disorderly arranged, and swollen in varying degrees (mildly, moderately, or severely), inside of which vacuoluses are formed; the myofilaments are essentially in normal arrangement, and they undergo focal lysis in part of the cardiocytes; fuzzy transverse striations can be observed in local areas, and Z-lines are essentially normal, a few of which are disorderly arranged; interstitial collagen fibers have no significant proliferation.

Figure 5:
FIG. 5. Changes in ultramcirostructure of cardiac muscle tissues from the losartan group.
Figure 6:
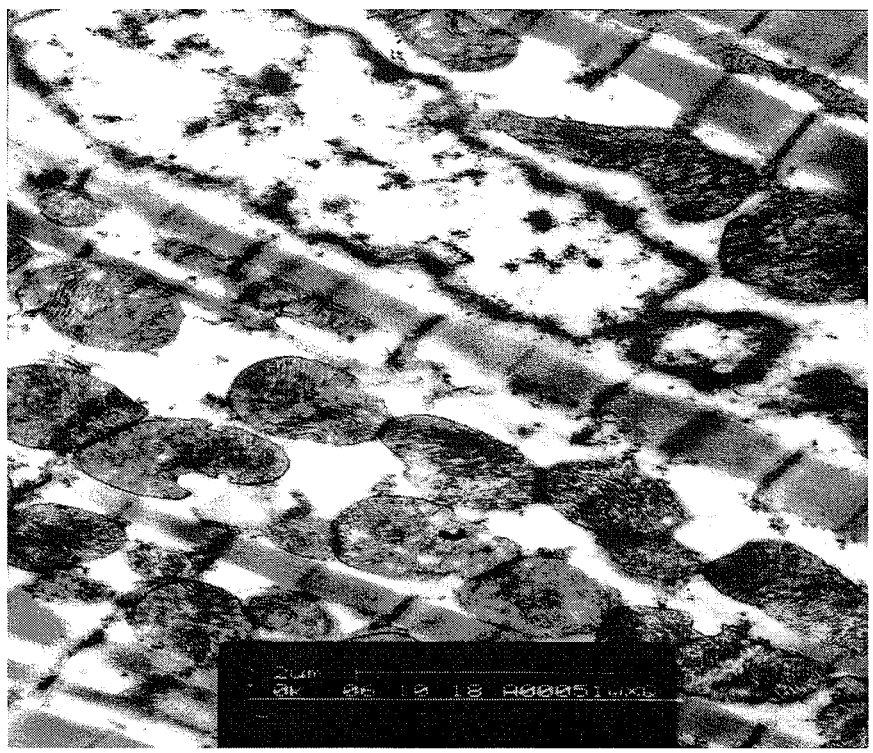
FIG. 6. Changes in ultramcirostructure of cardiac muscle tissues from the heptacosapeptide group.

In the losartan group (FIG. 5): morphology of the cellular nucleus is essentially normal and somewhat irregular; myofilaments under the plasma membrane undergo focal lysis; mitochondria are swollen mildly; the sarcoplasmic reticulum is dilated and mildly swollen; the structure of the Z-line and transverse striation are essentially normal, In the heptacosapeptide group (FIG. 6): As compared to the SHR model group, the myocardial ultrastructure is significantly improved. The structure of the cardiocyte is essentially normal, that is, its cardiocyte sarcomere and myofilaments are essentially normal; transverse striations are clear; interstitial collagen fibers have no significant proliferation; Z-lines are orderly arranged; the mitochondria have no significant proliferation, some of which are mildly swollen; myofilaments undergo mild lysis; and endothelial cells in capillary vessels are normal.

Although the above Examples are disclosed herein, the embodiments of the present invention is not limited to the aforementioned Examples; various variations on the embodiments according to the present invention may be made without departing from the spirit of the invention and in any case will fall within the scope defined by the claims of the present invention.

REFERENCE

1. Cooper G 4th. Basic determinants of myocardial hypertrophy: a review of molecular mechanisms. Annu Rev Med, 1997, 48: 13-23.
2. Aoki H, Sadoshima J, Izumo S. Myosin light chain kinase mediates sarcomere organization during cardiac hypertrophy in vitro. Nat Med 2000, 6(2): 183-188.

3. McKinsey T A, Kass D A. Small-molecule therapies for cardiac hypertrophy: moving beneath the cell surface. Nat Rev Drug Discov. 2007; 6(8):617-635.
4. Mitchell J A, Ventura H O, Mehra M R. Early recognition and treatment of hypertensive heart disease. Curr Opin Cardiol. 2005; 20(4):282-289.
5. Jalili T, Carlstrom J, Kim S, Freeman D, Jin H, Wu T C, Litwin S E, David Symons J. Quercetin-supplemented diets lower blood pressure and attenuate cardiac hypertrophy in rats with aortic constriction. J Cardiovasc Pharmacol. 2006; 47(4):531-541.
6. Carlstrom J, Symons J D, Wu T C, Bruno R S, Litwin S E, Jalili T. A quercetin supplemented diet does not prevent cardiovascular complications in spontaneously hypertensive rats. J Nutr. 2007; 137(3): 628-633.
7. Niizeki T, Takeishi Y, Kitahara T, et al. Diacylglycerol Kinase zeta Rescues Galphaq-Induced Heart Failure in Transgenic Mice. Circ J. 2008; 72(2): 309-317.
8. Dorn G W 2nd, Tepe N M, Lorenz J N, Koch W J, Liggett S B. Low- and high-level transgenic expression of $\beta_2$-adrenergic receptors differentially affect cardiac hypertrophy and function in Gaq-overexpressing mice. Proc Natl Acad Sci USA. 1999; 96(11): 6400-6405.
9. Berenji K, Drazner M H, Rothermel B A, Hill J A. Does load-induced ventricular hypertrophy progress to systolic heart failure? Am J Physiol Heart Circ Physiol. 2005; 289 (1): H8-H16.

The invention claimed is:

1. A polypeptide consisting of SEQ ID NO: 3 or 4.
2. The polypeptide of claim 1, consisting of SEQ ID NO: 3.
3. The polypeptide of claim 1, consisting of SEQ ID NO: 4.
4. A formulation comprising the polypeptide of claim 1 and pharmaceutically acceptable additives.
5. The formulation of claim 4, wherein the formulation is configured for administration by parenteral injection.
6. The formulation of claim 4, wherein the polypeptide consists of SEQ ID NO: 3.
7. The formulation of claim 4, wherein the polypeptide consists of SEQ ID NO: 4.
8. A method of preparing the polypeptide of claim 1 comprising the step of:
   performing polypeptide synthesis in accordance with the amino acid sequence of the polypeptide of claim 1 in a polypeptide synthesizer.
9. A method of preparing the polypeptide of claim 1 comprising the steps of:
   ligating a nucleotide sequence encoding the polypeptide of claim 1 with a vector to form a recombinant vector;
   transforming said recombinant vector into a host cell;
   inducing said host cell to express said polypeptide; and
   separating said polypeptide.
10. The method of claim 9, wherein the said vector is plasmid pIVEX2.3MCS, and the said host cell is *Escherichia coli* strain BL21.
11. A method for treating myocardial hypertrophy, comprising administration of the polypeptide of claim 1.
12. The method of claim 11, wherein the administration of the polypeptide is conducted by a parenteral injection.
13. A method for treating myocardial hypertrophy, comprising administration of the polypeptide of claim 2.
14. A method for treating myocardial hypertrophy, comprising administration of the polypeptide of claim 3.

* * * * *